(12) United States Patent
Ikeda et al.

(10) Patent No.: US 12,048,683 B2
(45) Date of Patent: Jul. 30, 2024

(54) KAEMPFEROL ANALOG-CONTAINING COMPOSITION

(71) Applicant: OTSUKA PHARMACEUTICAL CO., LTD., Tokyo (JP)

(72) Inventors: Yasutaka Ikeda, Osaka (JP); Tsubasa Mizokami, Osaka (JP); Yasuhiro Abiru, Osaka (JP); Minoru Akiyama, Osaka (JP); Ayuko Oyama, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 17/228,374

(22) Filed: Apr. 12, 2021

(65) Prior Publication Data

US 2021/0228540 A1 Jul. 29, 2021

Related U.S. Application Data

(63) Continuation of application No. 16/642,189, filed as application No. PCT/JP2018/032104 on Aug. 30, 2018, now abandoned.

(30) Foreign Application Priority Data

Aug. 30, 2017 (WO) .................. PCT/JP2017/031214

(51) Int. Cl.
*A61K 31/353* (2006.01)
*A23L 29/00* (2016.01)
*A23L 29/30* (2016.01)
*A61K 31/7048* (2006.01)

(52) U.S. Cl.
CPC .......... *A61K 31/353* (2013.01); *A23L 29/035* (2016.08); *A23L 29/30* (2016.08); *A61K 31/7048* (2013.01)

(58) Field of Classification Search
None
See application file for complete search history.

(56) References Cited

U.S. PATENT DOCUMENTS

| | | | |
|---|---|---|---|
| 9,198,453 B2 * | 12/2015 | Zachwieja | A61P 21/00 |
| 9,675,580 B2 * | 6/2017 | Kim | A61K 31/352 |
| 2006/0111318 A1 * | 5/2006 | Okamoto | A61P 27/02 |
| | | | 514/170 |
| 2009/0098230 A1 | 4/2009 | Andrews | |
| 2014/0107193 A1 | 4/2014 | Kuang et al. | |
| 2016/0081973 A1 | 3/2016 | Kawase et al. | |
| 2018/0117000 A1 | 5/2018 | Toda et al. | |
| 2018/0289660 A1 | 10/2018 | Nabeshima et al. | |
| 2020/0323816 A1 | 10/2020 | Ikeda et al. | |

FOREIGN PATENT DOCUMENTS

| | | |
|---|---|---|
| CN | 101257897 A | 9/2008 |
| CN | 102138998 A | 8/2011 |
| CN | 102600269 A | 7/2012 |
| CN | 104223068 A | 12/2014 |
| CN | 104223068 B | 9/2016 |
| CN | 112568425 A | 3/2021 |
| EP | 2 907 517 A1 | 8/2015 |
| JP | 2006-298876 A | 11/2006 |
| JP | 2007-228855 A | 9/2007 |
| JP | 2008-013525 A | 1/2008 |
| JP | 2008-208041 A | 9/2008 |
| JP | 2009-155333 A | 7/2009 |
| JP | 2012-236793 A | 12/2012 |
| JP | 2013-542924 A | 11/2013 |
| KR | 10-1177786 B1 | 8/2012 |
| WO | 2007/008548 A2 | 1/2007 |
| WO | 2010/086972 A1 | 8/2010 |
| WO | 2012/037023 A1 | 3/2012 |
| WO | 2014/171333 A1 | 10/2014 |
| WO | 2016/149277 A1 | 9/2016 |
| WO | 2016/163245 A1 | 10/2016 |
| WO | 2017/053583 A1 | 3/2017 |
| WO | 2017/061614 A1 | 4/2017 |
| WO | 2017/104777 A1 | 6/2017 |
| WO | 2019/043846 A1 | 3/2019 |
| WO | 2019/044964 A1 | 3/2019 |

OTHER PUBLICATIONS

English translation of International Preliminary Report on Patentability dated Aug. 25, 2021 of PCT/JP2020/007858.
Extended European search report dated Apr. 23, 2021, from the European Patent Office in European Application No. 18851739.5.
Williams J.H., et al., "Hemoglobin desaturation in highly trained athletes during heavy exercise", Med Sci Sports Exerc, 1986, 18: 168-173.
Relationship between Age, PaO, and Saturation retrieved from URL , https://geriatrictoolkit.missouri.edu/cv/SpO2.pdf, 2004.
Montero M., et al., "Direct activation of the mitochondrial calcium uniporter by natural plant flavonoids", Biochem. J., 2004, 384, 19-24.
Da-Silva W. S., et al., "The small polyphenolic molecule kaempferol increases cellular energy expenditure and thyroid hormone activation", Diabetes, 2007, 56: 767-776.
Baba, "Oxygen uptake efficiency slope (OUES): physiological background and clinical application", The Tokai Journal of Sports Medical Science, 1999, 11, 9-14.
English translation of PCT/ISA/210 (International Search Report) of PCT/JP2018/032104.
English translation of PCT/IB/373 (International Preliminary Report on Patentability) of PCT/JP2018/032104.
English translation of PCT/IB/373 (International Preliminary Report on Patentability) of PCT/JP2017/031214.
English translation of PCT/ISA/210 (International Search Report) of PCT/JP2020/007858.

(Continued)

*Primary Examiner* — Traviss C McIntosh, III
(74) *Attorney, Agent, or Firm* — Sughrue Mion, PLLC

(57) ABSTRACT

The present application provides a method for improvement in physical activity efficiency, a method for reducing fatigue, and a method for improving dynamic/kinetic visual acuity, comprising administering a composition comprising a kaempferol analog to a subject in need thereof.

15 Claims, 16 Drawing Sheets

(56) References Cited

OTHER PUBLICATIONS

Habbu P. V., et al., "Adaptogenic and in vitro antioxidant activity of flavanoids and other fractions of *Argyreia speciosa* (Burm. f) Boj. in acute and chronic stress paradigms in rodents", Indian Journal of Experimental Biology, 2010, 48, 53-60.

Bilyk A., et al., "Distribution of Quercetin and Kaempferol in Lettuce, Kale, Chive, Garlic Chive, Leek, Horseradish, Red Radish, and Red Cabbage Tissues", J. Agric. Food Chem., 1985,.33, 226-228.

Adam K. P., "Phenolic constituents of the fern Phegopteris connectilis", Phytochemistry, 1999, 52, 929-934.

Extended European Search Report dated Oct. 21, 2022 issued by European Patent Office in European Application No. 20763421.3, corresponding to U.S. Appl. No. 17/433,904.

J.M. Calderon-Montano et al., "A Review on the Dietary Flavonoid Kaempferol", Mini-Reviews in Medicinal Chemistry, 2011, vol. 11, pp. 298-344 (47 pages total).

Search Report and Written Opinion dated May 19, 2023 from the Intellectual Property Office of Singapore in Singapore Application No. 11202109239V, corresponding to U.S. Appl. No. 17/433,904.

Friedman L., "Saffron Improves Vision in Aging Humans", Life Extension Magazine, Jul. 2016, pp. 1-9 (9 total pages).

Menayang A., "Noni leaf extract delayed fatigue in swimmers (rodent ones, at least)", Natural Ingredients, Aug. 18, 2016, pp. 1-4 (4 total pages).

Ayaz F. A. et al., "Phenolic acid contents of kale (*Brassica oleraceae* L. var. acephala DC.) extracts and their antioxidant and antibacterial activities", Food Chemistry, Mar. 1, 2008, vol. 107, No. 1, pp. 19-25 (8 total pages).

Lee J.- J. et al., "The effects of *Brassica juncea* L. leaf extract on obesity and lipid profiles of rats fed a high-fat/high-cholesterol diet", Nutrition Research and Practice, Jul. 18, 2018, vol. 12, No. 4, pp. 298-306 (9 total pages).

"9 Benefits of Arugula", EcoWatch, Jun. 30, 2014, pp. 1-7 (7 total pages), Obtained from: https://www.ecowatch.com/9-benefits-of-arugula-1881929191.html.

International Search Report of PCT/JP2022/025267 dated Aug. 23, 2022 [PCT/ISA/210].

Klaus-Peter Adam, "Phenolic constituents of the fern Phegopteris connectilis", Phytochemistry, 52, 1999, pp. 929-934. (Year: 1999).

Stephan Sorichter et al., "Skeletal troponin I as a marker of exercise-induced muscle damage", J. Appl. Physiol., 1997, pp. 1076-1082, vol. 83, No. 4.

U.S. Appl. No. 18/573,785, filed Dec. 22, 2023 (Koichi Okita et al).

\* cited by examiner

KAEMPFEROL ANALOG-CONTAINING COMPOSITION

CROSS REFERENCE TO RELATED APPLICATIONS

This application is a Continuation of U.S. application Ser. No. 16/642,189 filed Feb. 26, 2020, which is a National Stage of International Application No. PCT/JP2018/032104 filed Aug. 30, 2018, claiming priority based on International Application No. PCT/JP2017/031214 filed Aug. 30, 2017. The contents of the prior applications are incorporated herein in their entirety.

TECHNICAL FIELD

The present application relates to a composition for improvement in physical activity efficiency, a composition for reducing fatigue, and a composition for improving dynamic/kinetic visual acuity.

BACKGROUND ART

Improvement of physical activity efficiency, reduction of fatigue, and improvement in dynamic/kinetic visual acuity are very important not only in athletes with intense training but also in ordinary people's daily work (e.g. housework, baggage handling, stair climbing). Oxygen consumption is an indicator of energy production, and improving oxygen consumption efficiency is key to achieving a sustained "physical activity" in sports and daily life without feeling tired or breathlessness.

Arterial oxygen saturation at rest is generally considered normal at 96% or higher, but decreases to 93-88% during strenuous exercise (Non-Patent Document 1). Arterial oxygen saturation (at rest) is about 97% in people in their 20s, but this value decreases with age, reaching about 93% in people in their 60s (Non-Patent Document 2). In other words, in addition to the rapid decline in oxygen status during intense sports, the decline in oxygen status may also occur in the daily lives of ordinary people due to aging, labor, bad weather (atmospheric depression), apnea syndrome and the like.

Since the decline in the oxygen state can occur not only in sports but also in the daily life of ordinary people, it is desired to provide a preparation which can improve the oxygen consumption efficiency, improve the physical activity efficiency, reduce the fatigue, or improve the dynamic/kinetic visual acuity, at the declined oxygen state in addition to at the normal oxygen state, and which can be taken safely on a daily basis.

Kaempferol is a kind of natural flavonoid contained in various edible plants, such as tea, broccoli, grapefruit, cabbage, kale, beans, *Cichorium endivia*, leek, tomato, strawberry, grape, Brussels sprouts, apple, quinoa, and horseradish.

Natural flavonoids, including kaempferol, have been studied with a focus on their diverse physiological effects, including the involvement of kaempferol in mitochondrial function (Patent Document 1, Patent Document 2, and Non-Patent Document 3) and the effects of kaempferol on cellular energy expenditure and thyroid hormone (Non-Patent Document 4), all of which relate to in vitro studies.

Patent Document 3 discloses the effect of quercetin on lactic acid concentration, but there is no specific disclosure using other flavonoids.

PRIOR ART DOCUMENT

Patent Document

Patent Document 1: WO 2014/171333
Patent Document 2: JP 2007-228855 A
Patent Document 3: JP 2013-542924 A

Non-Patent Document

Non-Patent Document 1: Williams J H, Powers S K, Stuart M K (1986) Hemoglobin desaturation in highly trained athletes during heavy exercise. Med Sci Sports Exerc 18: 168-173.
Non-Patent Document 2: Relationship between Age, PaO, and Saturation retrieved from URL <https://geriatrictoolkit.missouri.edu/cv/SpO2.pdf>.
Non-Patent Document 3: M. Montero, C. D. Lobaton, E. Hernandez-Sanmiguel, et al., Direct activation of the mitochondrial calcium uniporter by natural plant flavonoids, Biochem. J. 384 (2004) 19-24.
Non-Patent Document 4: da-Silva W S, Harney J W, Kim B W, Li J, Bianco S D, Crescenzi A, Christoffolete M A, Huang S A, Bianco A C 2007 The small polyphenolic molecule kaempferol increases cellular energy expenditure and thyroid hormone activation. Diabetes 56:767-776.
Non-Patent Document 5: "Oxygen uptake efficiency slope (OUES): Sono seirigaku-teki kiso to rinshŏ ŏyŏ" [Oxygen uptake efficiency slope (OUES): its physiological basis and clinical application], The Tokai journal of sports medical science 11, 9-14, 1999-03, Tokai University (in Japanese).

The disclosures of the prior art documents cited herein are hereby incorporated by reference in their entirety.

SUMMARY

Technical Problem

An object of the present application is to provide a composition which can improve oxygen consumption efficiency (that is, the ability to use oxygen can be enhanced.), and thereby can suppress a decrease in physical activity efficiency, improve physical activity efficiency, or reduce fatigue, or which can suppress a decrease in dynamic/kinetic visual acuity, or improve dynamic/kinetic visual acuity, even at the lowered oxygen state in addition to the normal oxygen state.

Solution to Problem

The present inventors have been intensively studied to solve the above problems, and have found that oral administration of a kaempferol-containing composition to a human increases oxygen consumption efficiency, improves physical activity efficiency, reduces fatigue feeling, and improves dynamic/kinetic visual acuity, in a wide range of an exercise ranging from mild exercise of the level of daily work to an exercise of the level of intense sports, thereby reaching the present invention.

The present invention provides the following:

[1] A composition for improvement in physical activity efficiency, comprising a kaempferol analog of Formula I:

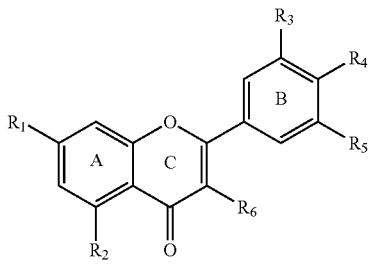

or a glycoside thereof, wherein:
$R_1$ is —OH, or —OCH$_3$;
$R_2$ is H, or —OH;
$R_3$ is H, —OH, or —OCH$_3$;
$R_4$ is —OH, or —OCH$_3$;
$R_5$ is H, or —OH; and
$R_6$ is H, —OH, or —OCH$_3$;
excluding the following compound:

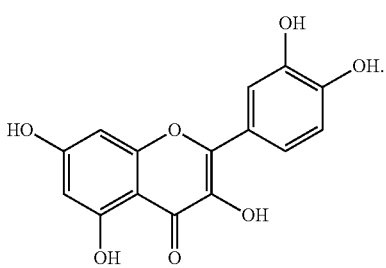 [SMILES: O=c1c(O)c(-c2ccc(O)c(O)c2)oc2cc(O)cc(O)c12]

[2] The composition according to [1], wherein the improvement in physical activity efficiency is improvement in endurance.

[3] The composition according to [1], wherein the improvement in physical activity efficiency is reduction of breathlessness.

[4] A composition for reducing fatigue, comprising a kaempferol analog of Formula I:

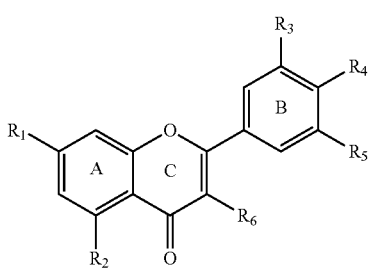

or a glycoside thereof, wherein:
$R_1$ is —OH, or —OCH$_3$;
$R_2$ is H, or —OH;
$R_3$ is H, —OH, or —OCH$_3$;
$R_4$ is —OH, or —OCH$_3$;
$R_5$ is H, or —OH; and
$R_6$ is H, —OH, or —OCH$_3$;

excluding the following compound:

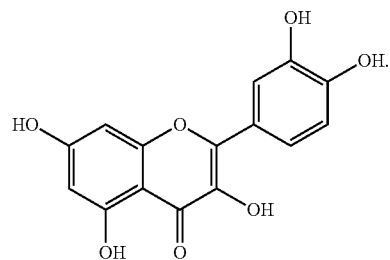 [SMILES: O=c1c(O)c(-c2ccc(O)c(O)c2)oc2cc(O)cc(O)c12]

[5] A composition for improving dynamic/kinetic visual acuity, comprising a kaempferol analog of Formula I:

(I)

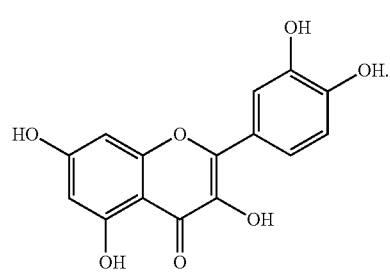 [SMILES: O=c1c(O)c(-c2ccc(O)c(O)c2)oc2cc(O)cc(O)c12]

or a glycoside thereof, wherein:
$R_1$ is —OH, or —OCH$_3$;
$R_2$ is H, or —OH;
$R_3$ is H, —OH, or —OCH$_3$;
$R_4$ is —OH, or —OCH$_3$;
$R_5$ is H, or —OH; and
$R_6$ is H, —OH, or —OCH$_3$;
excluding the following compound:

[6] The composition according to any one of [1] to [5], wherein the glycoside of kaempferol analog is represented by Formula I, wherein:
at least one selected from $R_1$, $R_2$, $R_4$, and $R_6$ is independently selected from —OR$_7$, —OR$_7$R$_8$, and —OR$_7$R$_8$R$_9$;
$R_7$ is a glucose residue; and
$R_8$ and $R_9$ are independently selected from a glucose residue, a mannose residue, a galactose residue, a fucose residue, a rhamnose residue, an arabinose residue, a xylose residue, a fructose residue, a glucuronic acid residue, and an apiose residue.

[7] The composition according to any one of [1] to [6], wherein the kaempferol analog or a glycoside thereof is selected from the group consisting of the following:

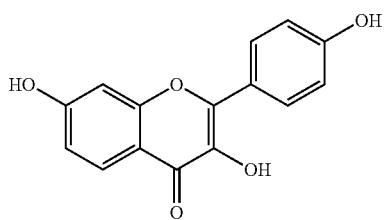
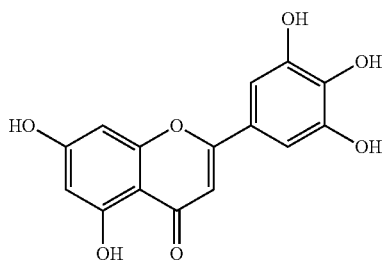
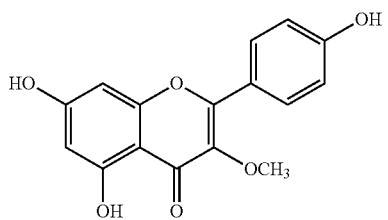
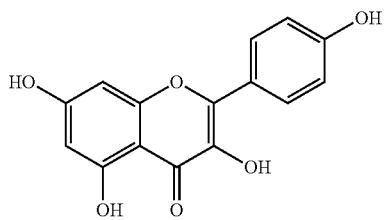
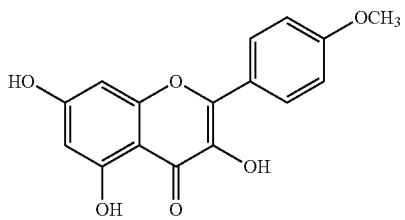
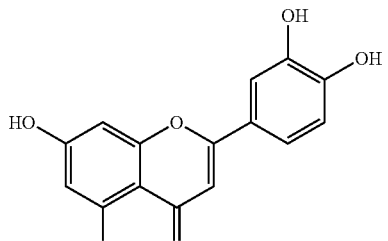
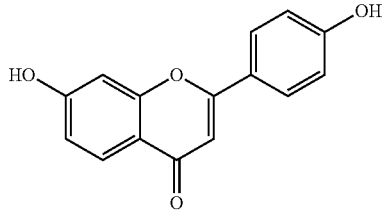

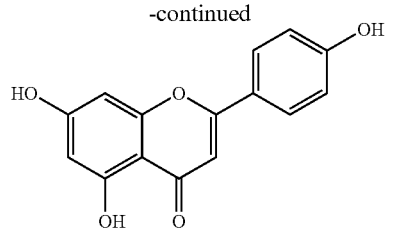
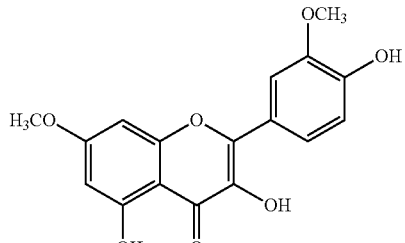
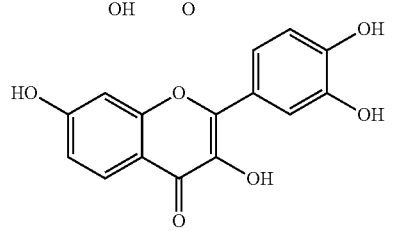
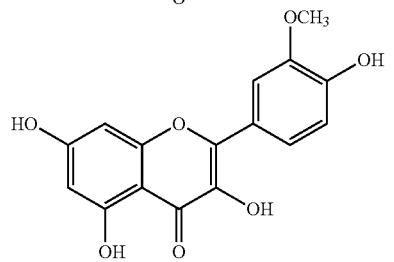

and a glycoside thereof.

[8] The composition according to any one of [1] to [7], wherein the kaempferol analog or a glycoside thereof is kaempferol or kaempferol 3-O-glucoside.

[9] The composition according to any one of [1] to [8], comprising 0.1 to 200 mg (kaempferol analog equivalent value) of the kaempferol analog or a glycoside thereof.

[10] The composition according to any one of [1] to [9], comprising 0.5 mg to 100 mg (kaempferol analog equivalent value) of the kaempferol analog or a glycoside thereof.

[11] The composition according to any one of [1] to [10], wherein said composition is for administration at a dose of 0.1 mg to 200 mg (kaempferol analog equivalent value) of the kaempferol analog or a glycoside thereof per administration.

[12] The composition according to any one of [1] to [11], wherein said composition is for administration at a dose of 0.5 mg to 100 mg (kaempferol analog equivalent value) of the kaempferol analog or a glycoside thereof per administration.

[13] The composition according to any one of [1] to [12], wherein said composition is for administration at a dose of 0.1 mg to 600 mg (kaempferol analog equivalent value) of the kaempferol analog or a glycoside thereof per day.

[14] The composition according to any one of [1] to [13], wherein said composition is for administration at a dose of 0.5 mg to 200 mg (kaempferol analog equivalent value) of the kaempferol analog or a glycoside thereof per day.

[15] The composition of any one of [1] to [14], wherein said composition is for administration to a subject who is hypoxic.

[16] The composition according to any one of [1] to [15], wherein said composition is a food and drink.

[17] The composition according to any one of [1] to [15], wherein said composition is a pharmaceutical composition.

Furthermore, the present invention provides use of a kaempferol analog or a glycoside thereof in the manufacture of a composition for improvement in physical activity efficiency, a composition for reducing fatigue, or a composition for improving dynamic/kinetic visual acuity.

Furthermore, the present invention provides a method for improvement in physical activity efficiency, a method for reducing fatigue, or a method for improving dynamic/kinetic visual acuity, comprising administering a kaempferol analog or a glycoside thereof.

In addition, the present invention provides a kaempferol analog or a glycoside thereof for use in improvement in physical activity efficiency, reducing fatigue, or improving dynamic/kinetic visual acuity.

Effect of Invention

The composition of the present invention may improve oxygen consumption efficiency (an ability to utilize oxygen), thereby allowing for increased efficiency in any "physical activity" including daily activities and sports. For example, the composition of the present invention may allow for an exercise with a reduced breathlessness or an improved endurance. The composition of the present invention may also be used as a composition for reducing breathlessness or a composition for improving endurance. In addition, the composition of the present invention may reduce fatigue, and may allow for performing sports, daily housework, etc. without feeling fatigue. Furthermore, the composition of the present invention may improve dynamic/kinetic visual acuity and may contribute to an improved outcome, for example in sports.

BRIEF DESCRIPTION OF DRAWINGS

FIG. 6-1 depicts a graph showing the exercise intensity (% HR) and the rating of perceived exertion (RPE) at the oxygen consumption equivalent to the level of climbing stairs.

FIG. 6-2 depicts a graph showing the exercise intensity (% HR) and the rating of perceived exertion (RPE) at the oxygen consumption equivalent to the level of jogging.

FIG. 9-1 depicts a graph showing the ATP content in the soleus muscle (Sol).

FIG. 9-2 depicts a graph showing the ATP content in the whole brain.

DESCRIPTION OF EMBODIMENTS

Figure 1:
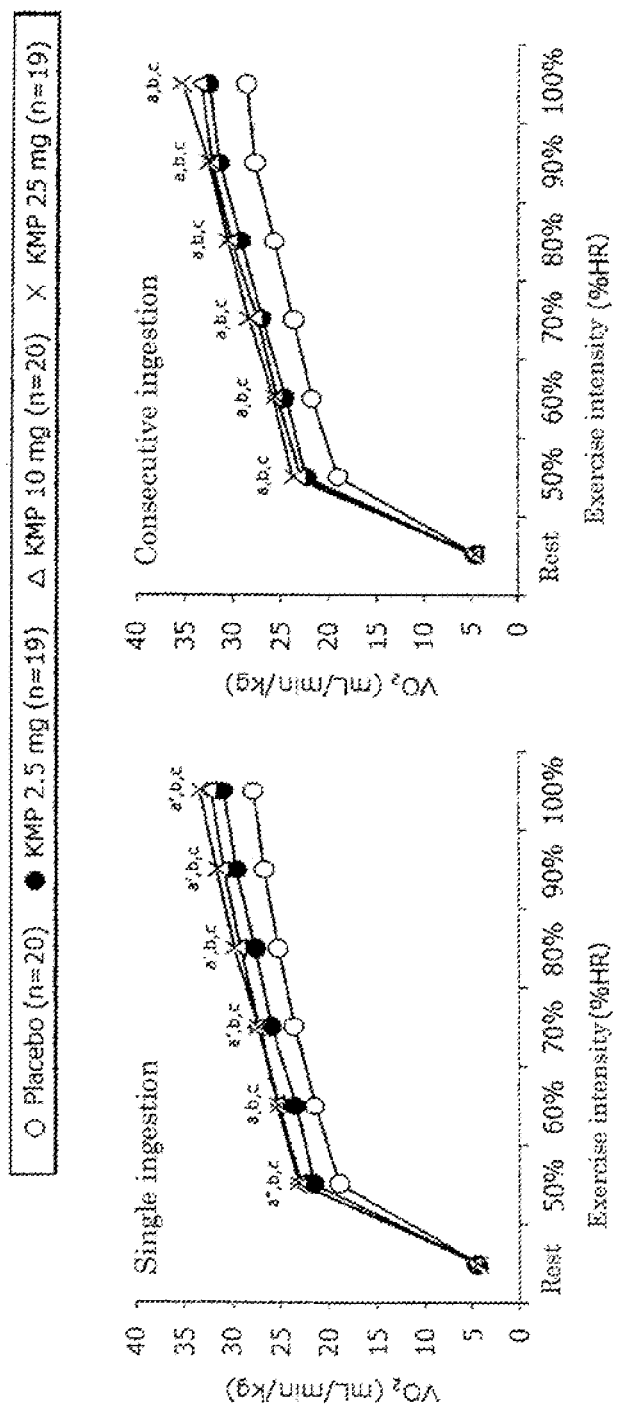
FIG. 1 depicts a graph showing the oxygen consumption ($VO_2$) at each exercise intensity.

The invention relates to a composition for improvement in physical activity efficiency, a composition for reducing fatigue, or a composition for improving dynamic/kinetic visual acuity, comprising a kaempferol analog or a glycoside thereof.

In the composition of the present invention, a kaempferol analog is a compound of Formula I:

(I)

[Chemical structure of Formula I with substituents $R_1$, $R_2$, $R_3$, $R_4$, $R_5$, $R_6$ on rings A, B, C]

wherein:
$R_1$ is —OH, or —OCH$_3$;
$R_2$ is H, or —OH;
$R_3$ is H, —OH, or —OCH$_3$;
$R_4$ is —OH, or —OCH$_3$;
$R_5$ is H, or —OH; and
$R_6$ is H, —OH, or —OCH$_3$;
excluding the following compound:

[Chemical structure of quercetin]

The composition of the present invention may comprise glycoside(s) of the kaempferol analog(s). Since the glycoside(s) of the kaempferol analog(s) may be converted into their aglycone(s) in vivo, they may have the same activity as the aglycone(s).

In the composition of the present invention, a glycoside of a kaempferol analogue means a compound in which a sugar chain having at least 1 (preferably 1 to 3, more preferably 1)

sugar residue is glycosidically bonded to at least 1 (preferably 1 to 2, more preferably 1) hydroxy group of the kaempferol analogue. Preferred examples of the sugar residue(s) include a glucose residue, a mannose residue, a galactose residue, a fucose residue, a rhamnose residue, an arabinose residue, a xylose residue, a fructose residue, a glucuronic acid residue, and an apiose residue.

More preferred examples of the glycoside(s) of the kaempferol analog(s) include compound(s) of Formula I, wherein at least one of $R_1$, $R_2$, $R_4$, and $R_6$ is independently selected from —$OR_7$, —$OR_7R_8$, and —$OR_7R_8R_9$;

$R_7$ is a glucose residue; and $R_8$ and $R_9$ are independently selected from a glucose residue, a mannose residue, a galactose residue, a fucose residue, a rhamnose residue, a arabinose residue, a xylose residue, a fructose residue, a glucuronic acid residue, and apiose residue.

Preferred examples of the kaempferol analog(s) and glycoside(s) thereof include the following kaempferol analog(s) and glycoside(s) thereof:

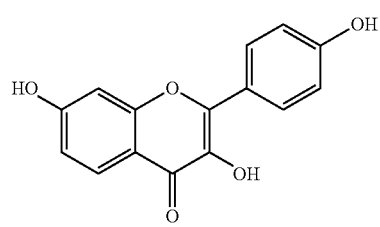

5-Deoxykaempferol

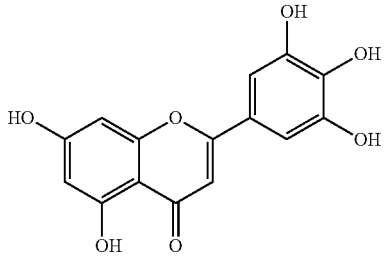

Tricetin

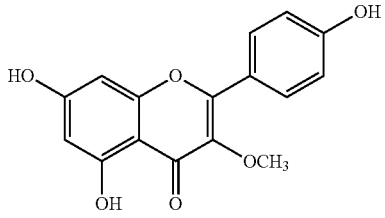

Isokaempferide

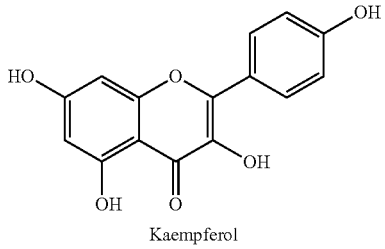

Kaempferol

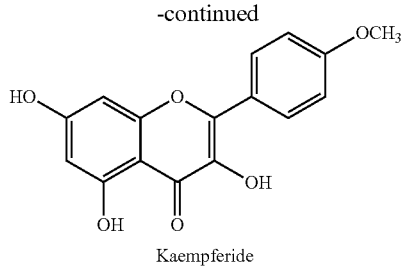

Kaempferide

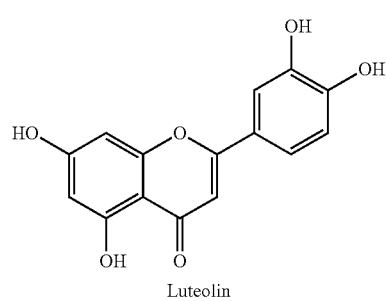

Luteolin

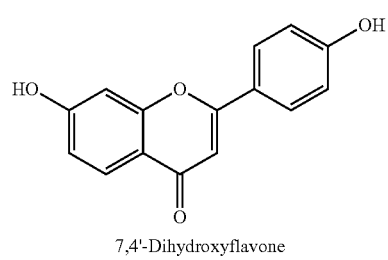

7,4'-Dihydroxyflavone

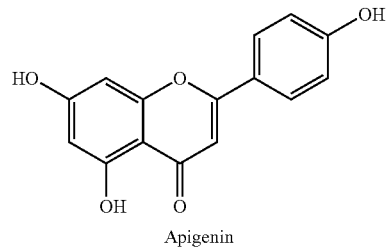

Apigenin

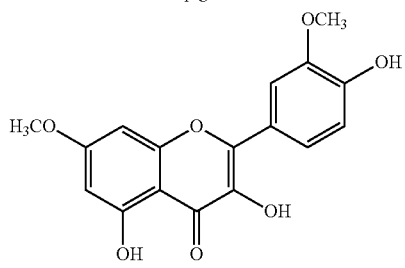

Rhamnazin

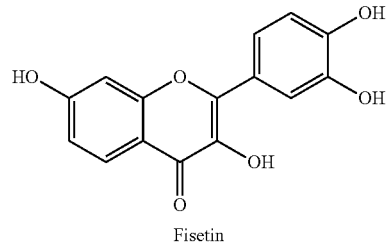

Fisetin

-continued

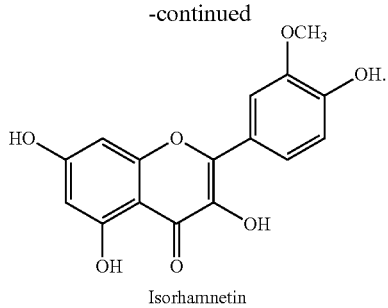

Isorhamnetin

More preferred examples of the kaempferol analog(s) include kaempferol, and examples of its glycoside(s) include kaempferol 3-O-glucoside.

In the composition of the present invention, a kaempferol analog or a glycoside thereof may be a combination of kaempferol analog(s) and glycoside(s) of kaempferol analog(s).

In the composition of the present invention, a kaempferol analog may be a single kind of kaempferol analog or a combination of a plurality of kinds of kaempferol analog (s).

In the composition of the present invention, a glycoside of a kaempferol analogue may be a single kind of glycoside of a kaempferol analogue or a combination of a plurality of kinds of glycoside(s) of kaempferol analog(s).

A kaempferol analog or a glycoside thereof used in the composition of the present invention is not limited in any way by its form, method of production or the like. For example, when kaempferol is selected, an extract from a plant known to contain a large amount of kaempferol, prepared by a known method may be used as it is, or a synthetic product may be used. The glycoside(s) of the kaempferol analogue(s) derived from such plant may be used as it is or may be converted into aglycone(s) (kaempferol analogue(s)), by a known method (For example, by enzymatic treatment). In the case of a food and drink or a pharmaceutical composition, it is preferable to use a product with a higher content obtained by a process (such as concentration or purification) allowing for blending an effective amount. In such a case, a known method of concentration or of purification can be used.

In the present specification, "kaempferol analog equivalent value" means a value obtained by converting the amount of the glycoside of the kaempferol analog into the amount of the kaempferol analog as its aglycone. Specifically, the kaempferol analog equivalent value can be calculated by multiplying the amount of substance of the glycoside, which is obtained by dividing the amount of the glycoside by its molecular weight, by the molecular weight of the aglycone.

The amount of kaempferol analog(s) or glycoside(s) thereof contained in the composition of the present invention (food and drink, pharmaceutical composition, etc.), the amount of kaempferol analog(s) or glycoside(s) thereof administered per administration, and the amount of kaempferol analog(s) or glycoside(s) thereof administered per day are not particularly limited as long as they are within the range in which the intended effect is exerted, and may be selected according to the form of the composition, the number of administrations, the health condition of the subject, etc. The administration period of the composition of the present invention is not particularly limited as long as it is within the range in which the intended effect is exerted, and may be administered as a single dose or continuously. In order to obtain a continuous effect of improvement in physical activity efficiency, reducing fatigue, or improving dynamic/kinetic visual acuity, the composition of the present invention may be desirably administered continuously over a long period of time, for example, 2 days, 3 days, 1 week, 10 days, 1 month, or 3 months or more.

Examples of the amount of kaempferol analog(s) or glycoside(s) thereof comprised in the composition of the present invention, as a kaempferol analog equivalent value(s), includes 0.1 mg to 200 mg, preferably 0.5 mg to 100 mg, more preferably 1 mg to 30 mg, and most preferably 2 mg to 10 mg, which may vary depending on the total weight of the composition. Examples of the lower limit of the amount of the kaempferol analog equivalent value include 0.1 mg, 0.5 mg, 1 mg, 2 mg, and 2.5 mg, and examples of the upper limit include 200 mg, 150 mg, 100 mg, 50 mg, 30 mg, 25 mg, 15 mg, 10 mg, 5 mg, 3 mg, and 2.5 mg, and a preferred range of the amount of the kaempferol analog equivalent value may be indicated by a combination of the upper and lower limits.

The compositions of the present invention may be such that kaempferol analog(s) or glycoside(s) thereof are administered, for example, 0.1 mg to 200 mg per administration, preferably 0.5 mg to 100 mg per administration, more preferably 1 mg to 30 mg per administration, and most preferably 2 mg to 10 mg per administration, as a kaempferol analog equivalent value. Examples of the lower limit of the dose of the kaempferol analog equivalent value per administration include 0.1 mg, 0.5 mg, 1 mg, 2 mg, and 2.5 mg, and examples of the upper limit include 200 mg, 150 mg, 100 mg, 50 mg, 30 mg, 25 mg, 15 mg, 10 mg, 5 mg, 3 mg, and 2.5 mg, and a preferred range of the dose of the kaempferol analog equivalent value per administration can be indicated by a combination of the upper and lower limits.

In the compositions of the present invention, kaempferol analog(s) or glycoside(s) thereof may be administered, for example, from 0.1 mg to 600 mg per day, preferably from 0.5 mg to 200 mg per day, more preferably from 1 mg to 100 mg per day, as a kaempferol analog equivalent value. Examples of the lower limit of the dose of the kaempferol analog equivalent value per day include 0.1 mg, 0.5 mg, 1 mg, 2 mg, and 2.5 mg, and examples of the upper limit include 600, 300, 200 mg, 150 mg, 100 mg, 50 mg, 30 mg, 25 mg, 15 mg, 10 mg, 5 mg, 3 mg, and 2.5 mg, and a preferred range of the dose of the kaempferol analog equivalent value per day may be indicated by a combination of the upper and lower limits. The dose of kaempferol analog(s) or glycoside(s) thereof which may be administered per day, may be administered in a single dose or in multiple divided doses (for example, twice, three times, four times, and five times).

The composition of the present invention is preferably formulated as oral dosage forms, and the form is not particularly limited, but may be conventional food forms such as tablets, granules, capsules, powders, chewable tablets, sweets (cookies, biscuits, chocolate confectioneries, chips, cakes, gums, candies, gummies, buns, yokan (sweet bean jelly), puddings, jellies, yogurt, ice cream, sherbet, etc.), breads, noodles, rice, cereal foods, beverages (liquid preparations, soft drinks, carbonated drinks, nutritional drinks, powdered drinks, fruit drinks, milk drinks, jelly drinks, etc.), soups (powder, freeze-dry), miso soups (powder, freeze-dry), and the like.

The composition of the present invention may be a food and drink or a pharmaceutical composition, and may be used as a food and drink, for example Foods with Functional Claims, Food for specified health uses, a health food, a nutritional supplement (supplement), a food for medical use, etc.

The compositions of the invention may be formulated into orally administered formulations by adding pharmaceutically acceptable base(s), carrier(s), and/or additive(s) usable in foods, etc., in addition to kaempferol analog(s) or glycoside(s) thereof. It is desirable that ingredients other than kaempferol analog(s) or glycoside(s) thereof used in the composition of the present invention do not impair the stability of the kaempferol analog(s), and that they do not impair the intended effect(s) of the composition of the present invention (for example, improved oxygen consumption, improved physical activity efficiency, reduced fatigue, or improved dynamic/kinetic visual acuity).

In the present invention, "improvement of oxygen consumption efficiency" means an increased ability to utilize oxygen. Specific examples include an increase in the oxygen consumption efficiency ($VO_2/VE$) described in the present Examples, and under a given exercise intensity an increase in oxygen consumption ($VO_2$), an increase in oxygen uptake efficiency slope (increase in OUES), and an increase in maximum oxygen consumption ($VO_{2peak}$).

As used herein, "physical activity" means a moving the body and includes any movements, for example daily housework, baggage handling, stair climbing, sports, and the like.

In the present invention, "improvement in physical activity efficiency" means that the body can be moved more easily in any kinds of physical activities. For example, improvement in physical activity efficiency includes continuing a physical activity for a long time in a more comfortable state by improving endurance, or doing a physical activity more easily in a state of reduced breathlessness. Examples of indices of improvement in physical activity efficiency include under a given exercise intensity, increased oxygen consumption ($VO_2$), increased oxygen consumption efficiency ($VO_2/VE$), increased oxygen uptake efficiency slope (increased OUES), increased maximum oxygen consumption ($VO_{2peak}$), increased maximum exercise load, decreased exercise intensity at a given oxygen consumption ($VO_2$), or decrease in rating of perceived exertion (these terms are described in Examples).

When the composition of the present invention is administered to improve physical activity efficiency, the dosage and the number of doses are not particularly limited, and the composition may be administered in the dosage, the number of doses and the period of administration exemplified above.

In the present invention, the term "reducing fatigue" means that any physical activity can be done while suppressing fatigue. Examples of indices of fatigue reduction include decreased exercise intensity or decrease in rating of perceived exertion (these terms are described in Examples). When the composition of the present invention is administered for reducing fatigue, the dosage and the number of doses are not particularly limited, and may be administered, for example, at the dose, the number of doses and the period of administration exemplified above.

In the present invention, improvement of dynamic/kinetic visual acuity means prevention of reduction of dynamic/kinetic visual acuity or improvement of dynamic/kinetic visual acuity. When the composition of the present invention is administered for improving dynamic/kinetic visual acuity, the dosage and the number of doses are not particularly limited, and the composition may be administered in the dosage, the number of doses and the period of administration exemplified above.

The composition of the present invention may have an effect of improving oxygen consumption efficiency (That is, the ability to use oxygen increases.). Therefore, the composition of the present invention may also be used for improving oxygen consumption efficiency.

In the present invention, the "hypoxic" state means a state in which oxygen level in the body is insufficient, for example, a state in which arterial oxygen saturation is less than 95%. Since the composition of the present invention may have an effect of improving oxygen consumption efficiency even in a subject in a hypoxic state, the composition of the present invention may contribute to improvement of physical activity efficiency, reduction of fatigue, and improvement of dynamic/kinetic visual acuity even in the subject in the hypoxic state.

The subject of administration of the composition of the present invention is not particularly limited, but is preferably human. It is preferable to administer the composition before and after sports, before and after outdoor work, before and after daily work (going up and down stairs, doing housework, etc.), when the subject feels that daily fatigue cannot be relieved, when the subject wants to work efficiently, or when the subject feels that the physical movement has become dull due to aging.

EXAMPLE

The present invention is explained in further detail with reference to Formulation Examples and Test Examples. However, the scope of the invention is not limited to these Examples.

| [Formulation Example 1] Cookies (kaempferol content: 2.5 mg) ||
|---|---|
| Quinua extract* | 37 wt % |
| Maple syrup | 22 wt % |
| Milk | 22 wt % |
| Salted butter | 15 wt % |
| Granulated sugar | 4 wt % |
| Total | 100 wt % |

According to a conventional method, these were mixed and baked at an oven temperature of about 140° C. for 20 minutes to produce cookies. The amount of kaempferol contained in one cookie was 2.5 mg (HPLC).

Quinoa extract*: an Quinoa extract wherein kaempferol glycosides were degraded into kaempferol aglycones by an enzymatic treatment.

| [Formulation Example 2] Capsule-shaped food (kaempferol content: 2.5 mg) ||
|---|---|
| Ethanol-extracted and enzyme-treated quinoa powder ** | 48 wt % |
| Gelatin Capsule | 52 wt % |
| Total | 100 wt % |

Gelatin Capsule was filled with Ethanol-extracted and enzyme-treated quinoa powder** to give the capsule food. The amount of kaempferol contained in one capsule was 2.5 mg (HPLC).

Ethanol-extracted and enzyme-treated quinoa powder**: prepared by process comprising: extracting quinoa grains with a 50% ethanol to give kaempferol glycosides, and then treating enzymatically to degrade the kaempferol glycosides into kaempferol aglycones.

Test Example 1: Incremental Loading Exercise Test with Bicycle

For 25 healthy adult males, 3 dosages of kaempferol-containing cookie-shaped foods (containing 2.5 mg, 10 mg, or 25 mg of kaempferol, respectively) and a placebo cookie-shaped food (kaempferol-free) were used as test foods, and a once-a-day ingestion for consecutive 8 days were repeated four times by the crossover method. 3 hours after a test food ingestion on day 1 (Single ingestion) and on day 8 (Consecutive ingestion), an incremental loading exercise with bicycle was performed while sampling the exhaled gas to determine the oxygen consumption. The Heart rate and the rating of perceived exertion were monitored during exercise. Dynamic/kinetic visual acuity was measured before and after the exercise. Details of each endpoint are given below.
<1: Evaluation of Oxygen Consumption ($VO_2$)>
Oxygen consumption ($VO_2$) (mL/min/kg) was calculated from the difference between the amount of oxygen in the inhaled gas (atmosphere) and the amount of oxygen in the exhaled gas. When a weight of the pedal approaches a subject's limit during incremental loading exercise with bicycle, a heart rate (HR) is maximized. The increase in heart rate from the resting heart rate to the maximum heart rate was defined as 100% of exercise intensity, and the oxygen consumption ($VO_2$) was plotted at each exercise intensity.

That is, for example, an exercise intensity of 50% HR is calculated by the following equation:

$$100\times(x-\text{Resting heart rate})/(\text{Maximum heart rate}-\text{Resting heart rate})=50\% \text{ HR},$$

and the oxygen consumption ($VO_2$) in which the heart rate is the "x" means "oxygen consumption ($VO_2$) at an exercise intensity of 50% HR".

The results are shown in FIG. 1.

As shown in FIG. 1, in both of the single ingestion and the consecutive ingestion, compared with the no intake of kaempferol, the intake of kaempferol showed the increased oxygen consumption at all exercise intensities (50%, 60%, 70%, 80%, 90%, and 100%).
<2: Evaluation of Oxygen Consumption Efficiency ($VO_2$/VE)>
Oxygen consumption efficiency was calculated by the following equation.

$$\text{Oxygen consumption efficiency } (VO_2/VE)=\text{oxygen consumption/ventilation}$$

Figure 2:
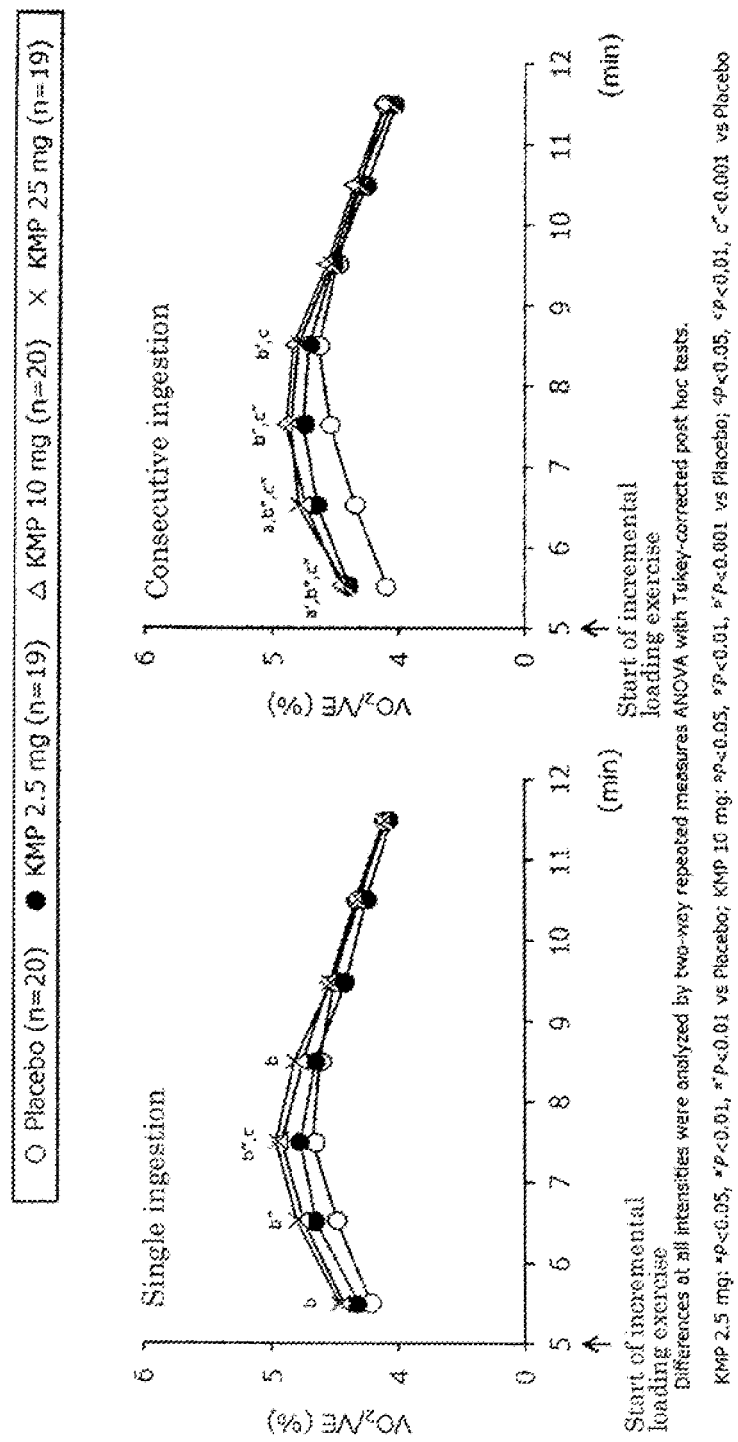
FIG. 2 depicts a graph showing the oxygen consumption efficiency ($VO_2/VE$) after initiation of incremental loading exercise.

As shown in FIG. 2, in both of the single ingestion and the consecutive ingestion, compared with the no intake of kaempferol, the intake of kaempferol showed the increased oxygen consumption efficiency ($VO_2$/VE).
<3: Evaluation of Oxygen Uptake Efficiency Slope (OUES)>
The oxygen uptake efficiency slope (OUES) was calculated using the ventilation and $VO_2$ every 1 min from the beginning of the incremental loading exercise. Specifically, a graph of linearity was obtained by plotting "logarithmic value of ventilation (VE)" on the horizontal axis and "$VO_2$" on the vertical axis, and the slope of the linear function graph was defined as OUES. For details, see Non-Patent Document 5.

Figure 3:
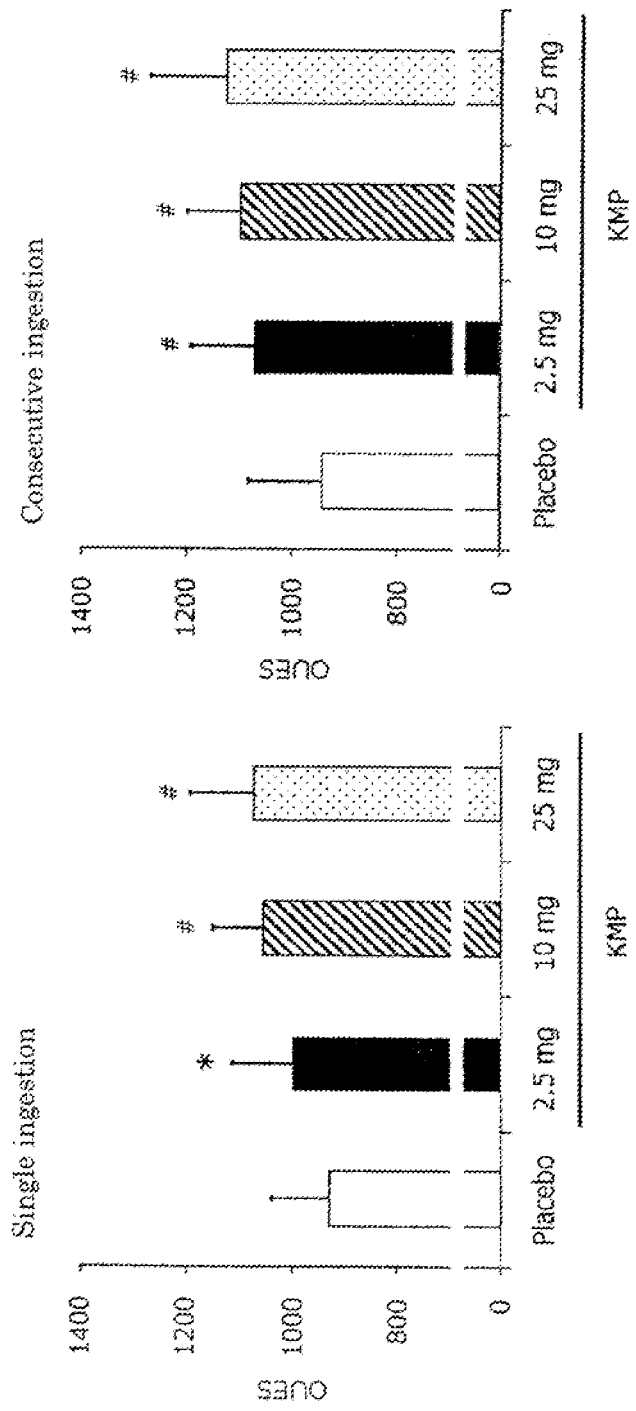
FIG. 3 depicts a graph showing the oxygen uptake efficiency slope (OUES) for each of the dosages in incremental loading exercise.
Figure 4:
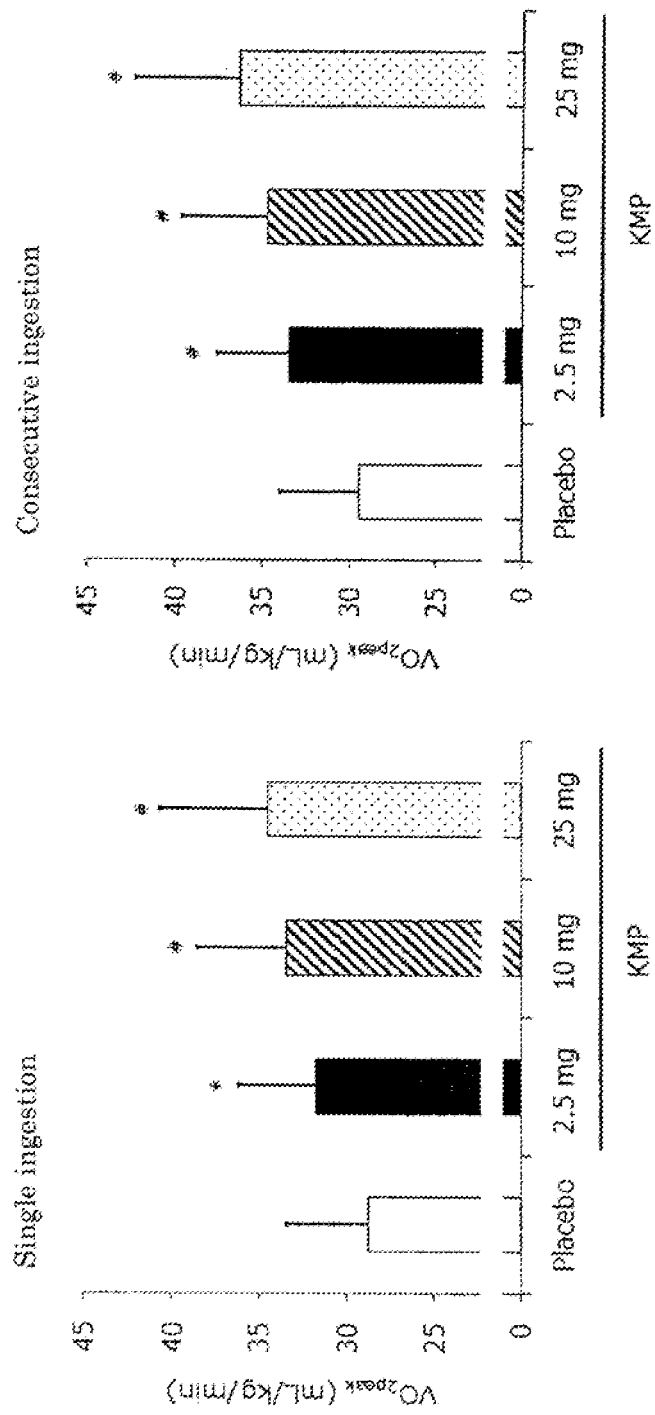
FIG. 4 depicts a graph showing the maximum oxygen consumption ($VO_{2peak}$) for each of the dosages in incremental loading exercise.
Figure 5:
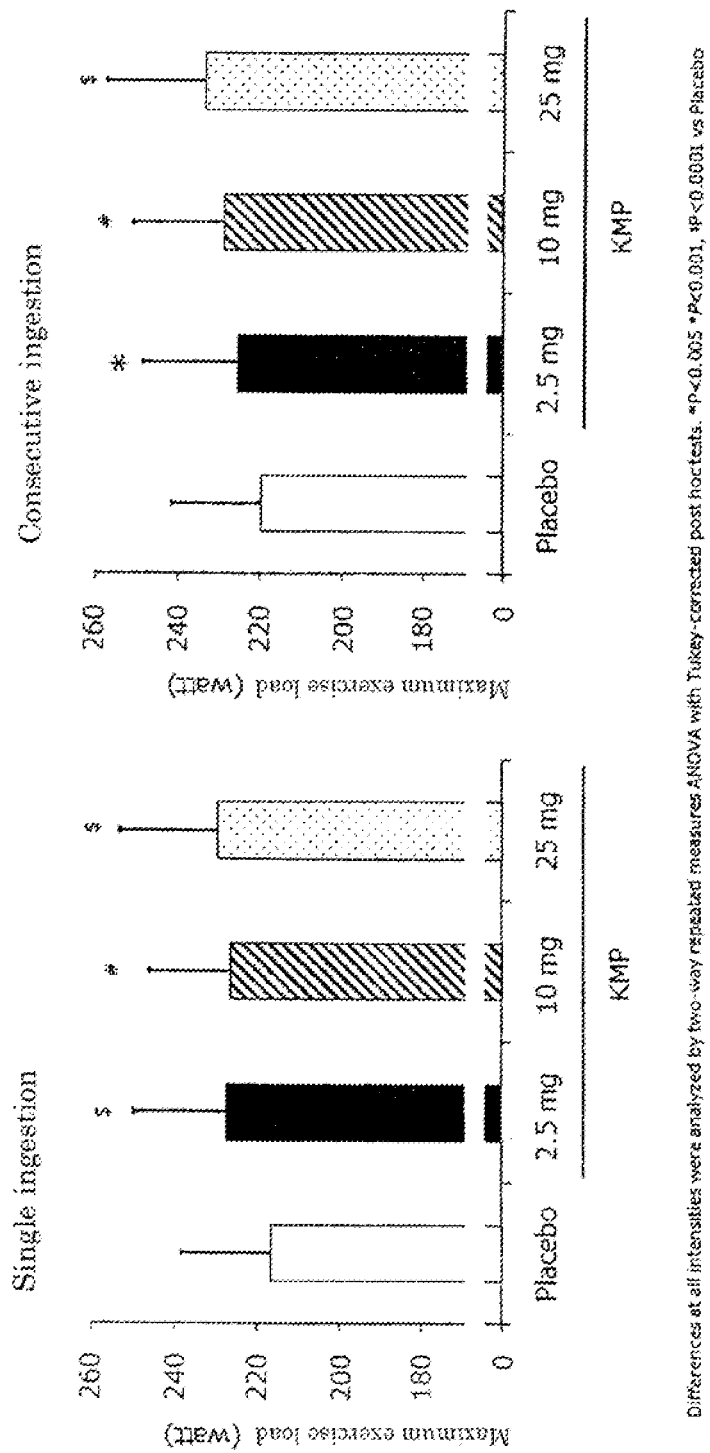
FIG. 5 depicts a graph showing the maximum exercise load for each of the dosages in incremental loading exercise.

As shown in FIG. 3, in both of the single ingestion and consecutive ingestion, compared with the no intake of kaempferol, the intake of kaempferol showed the increased oxygen uptake efficiency slope (OUES), which indicates that oxygen was more efficiently utilized during incremental loading exercise.
<4: Evaluation of Maximum Oxygen Consumption ($VO_{2peak}$)>
As shown in FIG. 4, in both of the single ingestion and consecutive ingestion, compared with the no intake of kaempferol, the intake of kaempferol showed the increased maximum oxygen consumption ($VO_{2peak}$) (mL/min/kg).
<5: Evaluation of the Maximum Exercise Load>
As shown in FIG. 5, in the both of the single ingestion and consecutive ingestion, compared with the no intake of kaempferol, the intake of kaempferol showed the increased maximum exercise load (Pedal Weight (watt))
<6: Effects on Exercise Intensity of the Level of Daily Work>
Oxygen consumption ($VO_2$) during stair climbing and jogging has been reported to be generally 14 mL/min/kg and 24.5 mL/min/kg, respectively.

Exercise intensity (% HR) and rating of perceived exertion (RPE) at the oxygen consumption ($VO_2$) of 14 mL/min/kg and 24.5 mL/min/kg in incremental loading exercise (the levels of stair climbing and jogging, respectively) were evaluated.

Figures 1, 6:
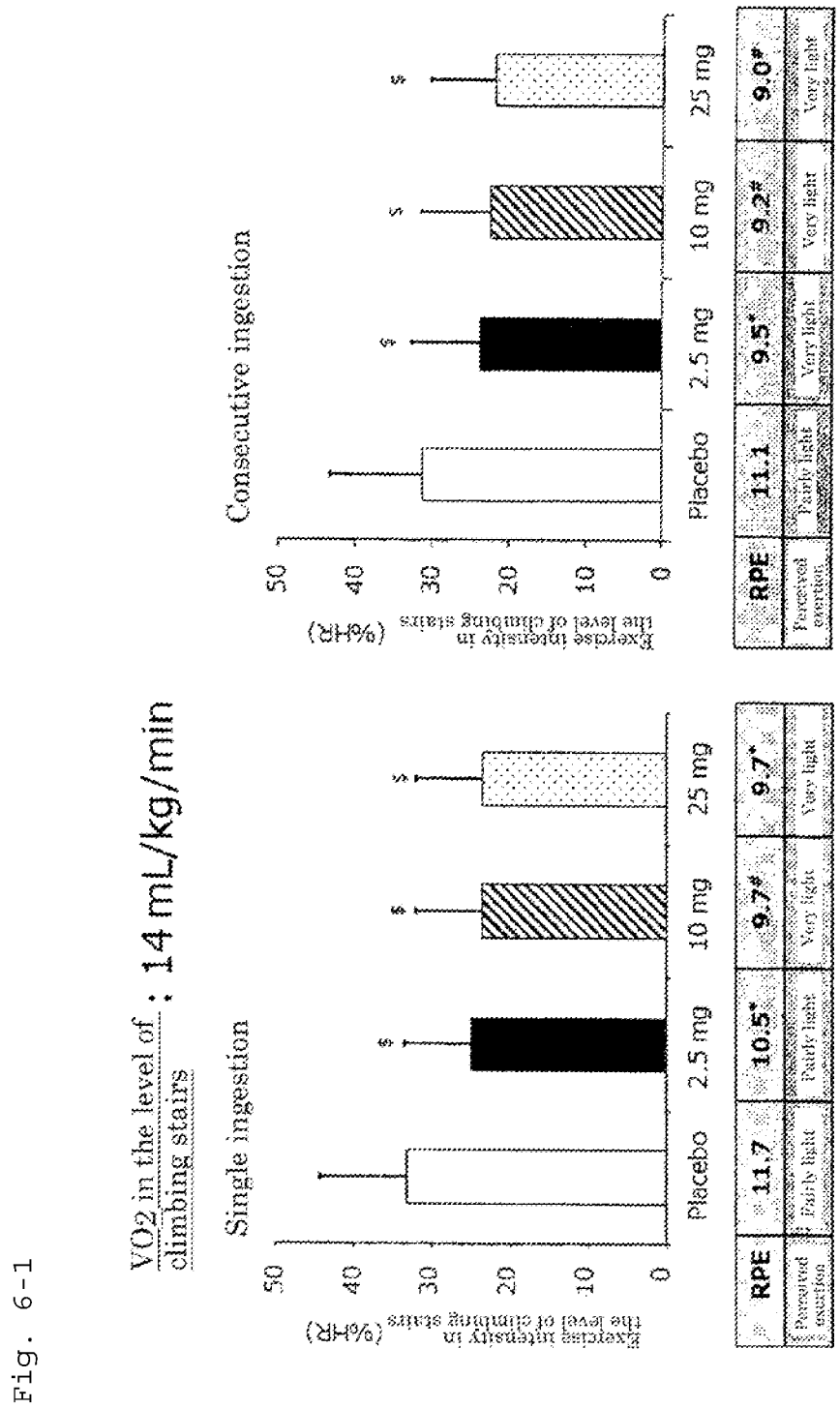
Figures 2, 6:
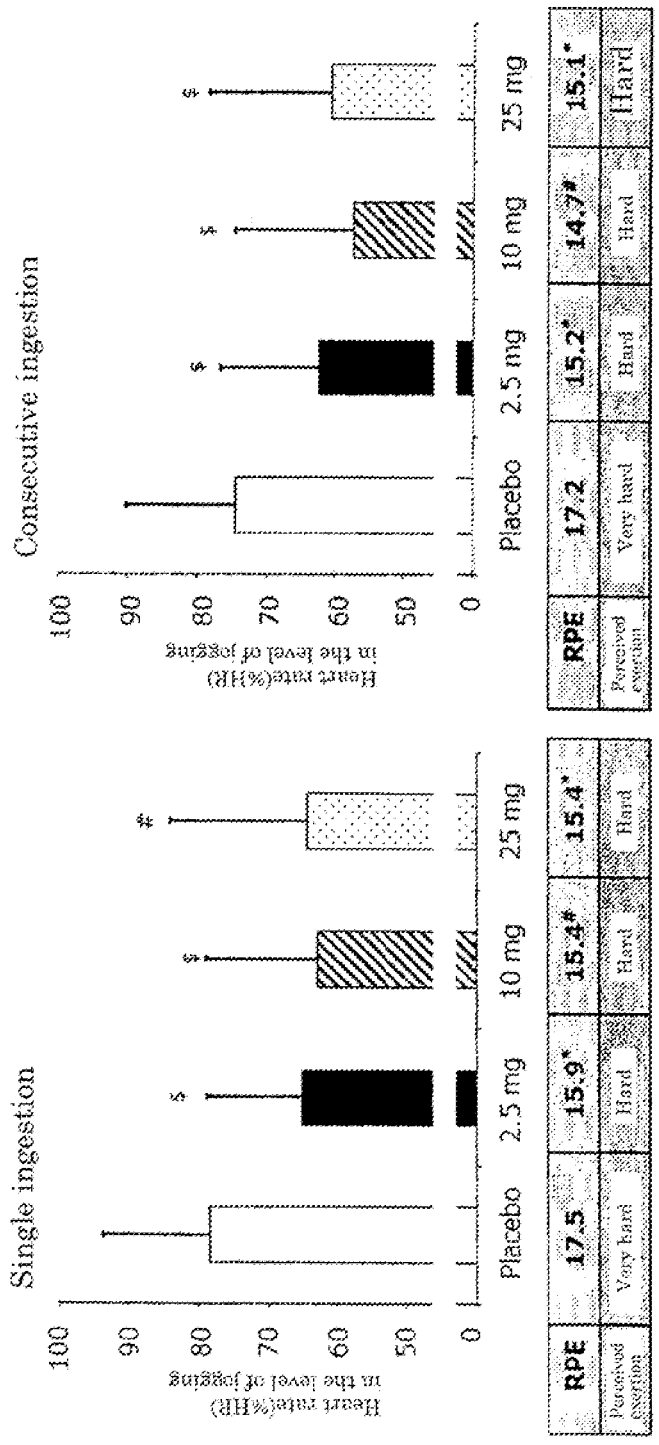

The calculation methods for oxygen consumption ($VO_2$) and exercise intensity (% HR) are the same as those described above. The perceived exertion was rated by the subject according to the following table at 1-minute intervals from the beginning of the incremental loading exercise, and the scales rated by each subject were averaged to give the rating of perceived exertion (RPE). As shown in FIGS. 6-1 and 6-2, in the both of the single ingestion and consecutive ingestion, compared with the no intake of kaempferol, the intake of kaempferol showed the decreased exercise intensity and the decreased rating of perceived exertion, at the both oxygen consumption ($VO_2$) levels (stair climbing and jogging).

| Scale | Perceived exertion |
|---|---|
| 20 | Maximally hard |
| 19 | Very very hard |
| 17 | Very hard |
| 15 | Hard |
| 13 | Somewhat hard |
| 11 | Fairly light |
| 9 | Very light |
| 7 | Very very light |
| 6 | Comfort |

As indicated in the results of the above 1 to 6, ingesting the kaempferol-containing food increased the oxygen consumption and the oxygen consumption efficiency at the same exercise intensities. In addition, the maximum exercise load increased. In addition, comparing the exercise intensities at the same oxygen consumption, it is found that the heart rate was decreased, which suggests that the subjects could exercise more comfortably with less breathlessness due to increased endurance. This improvement in physical activity efficiency may also reduce the fatigue of the subject. In fact, the ingestion of kaempferol-containing foods reduced perceived exertion and reduced breathlessness and fatigue. Therefore, it is suggested that the composition may be used for reducing breathlessness, and/or an enhancing endurance and/or improving oxygen consumption.

<7: Effect on Dynamic/Kinetic Visual Acuity>

Figure 7:
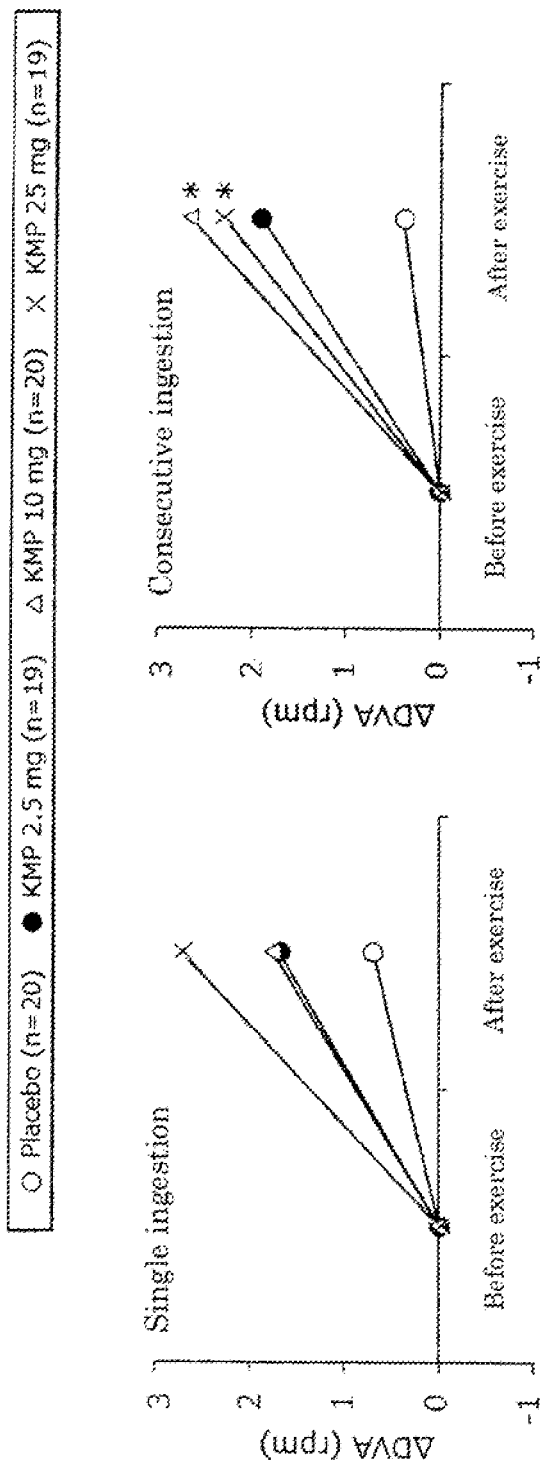
FIG. 7 depicts a graph showing the dynamic visual acuity (DVA) before and after incremental loading exercise.

The effect on dynamic/kinetic visual acuity was examined by measuring dynamic visual acuity (DVA) and kinetic visual acuity (KVA) before and after (within about 1 min after exercise) the incremental loading exercise.
(1) Measurement of Dynamic Visual Acuity (DVA)
Measurement Equipment:
Dynamic vision tester HI-10 Dynamic Vision Tester (Kowa Company, Ltd.)
Measurement Method:
The fastest visible speed of Landolt's ring moving horizontally on the arc was measured with the subject as the center. The target automatically decelerated gradually as it rotated, and when the subject detected the break in Landolt's ring, the subject pressed a switch on his/her hand to indicate the direction (up and down, and left and right) of the break. The number of revolutions at the time of the digital display was recorded on the recording paper and used as the inspection result. The results are shown in FIG. 7.

Test Example 2: Effect on ATP Production in Hypoxic Environment $C_2C_{12}$ skeletal muscle cells differentiated with horse serum were obtained, and various compounds (Final concentration of 20 μM) or dimethyl sulfoxide (DMSO) as a negative control were added thereto. After incubation in a hypoxic incubator (3% $O_2$) for 24 hours, the ATP content in the cells was determined using a kit (luciferase luminescence assay) manufactured by TOYO B-Net Co., Ltd. The ATP content of the negative control treated with DMSO was defined as 100%, and the activity value of the test compounds was calculated as a percentage based on the value of DMSO.

Figure 8:
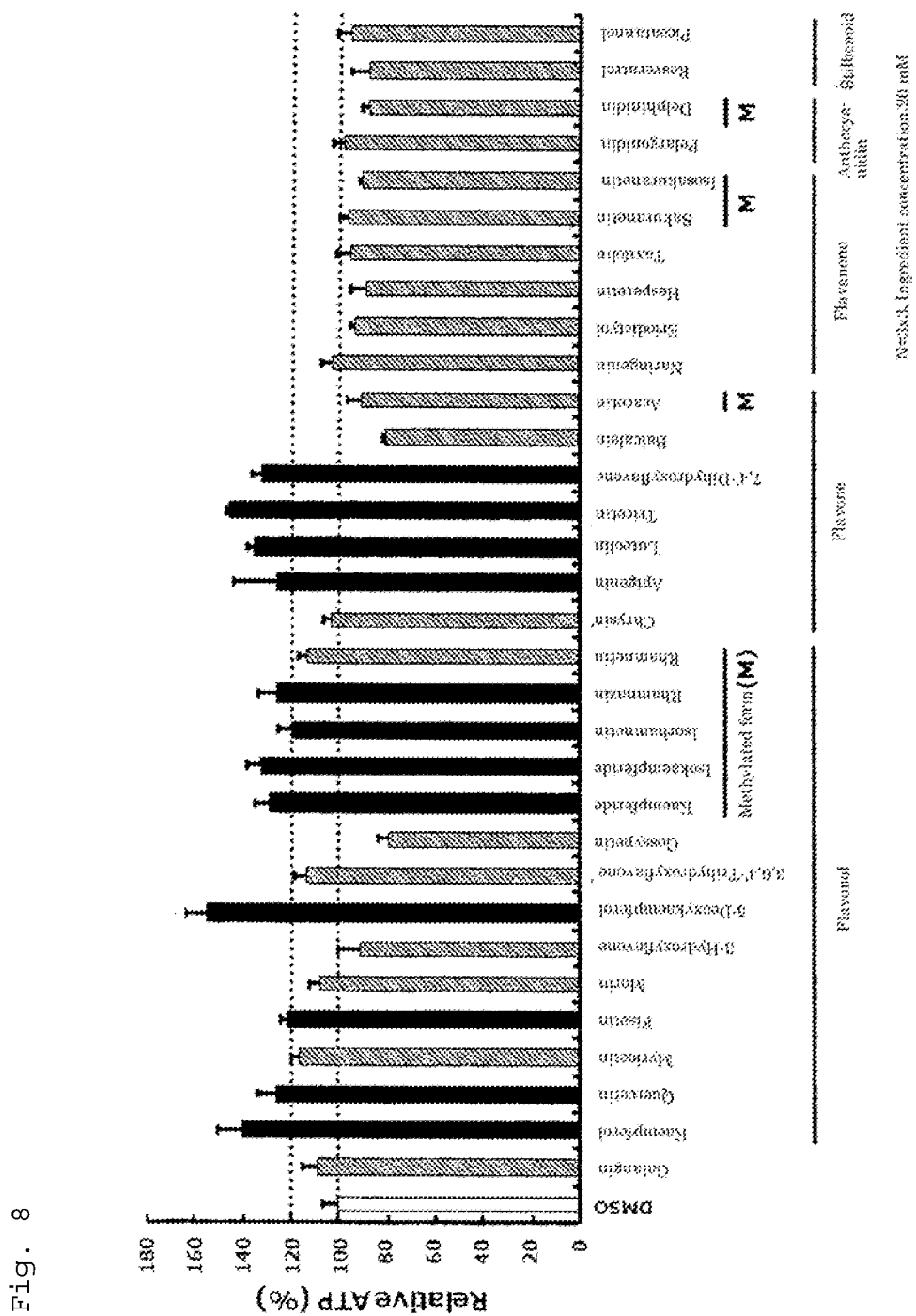
FIG. 8 depicts a graph showing the effect of each compound on ATP production in a hypoxic environment.

The results are shown in FIG. 8.

Test Example 3: Effect of Kaempferol or Kaempferol 3-O-Glucoside in Rat

Figures 1, 9:
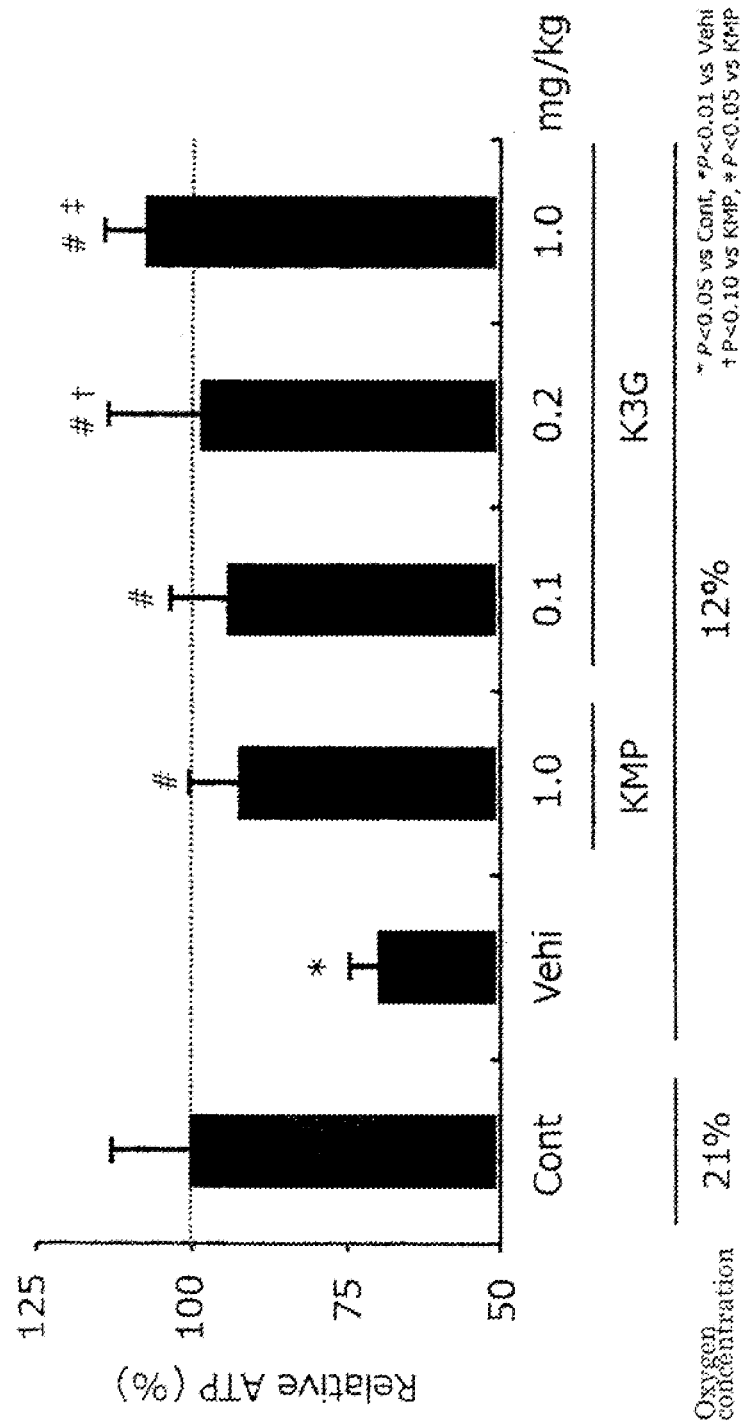
Figures 2, 9:
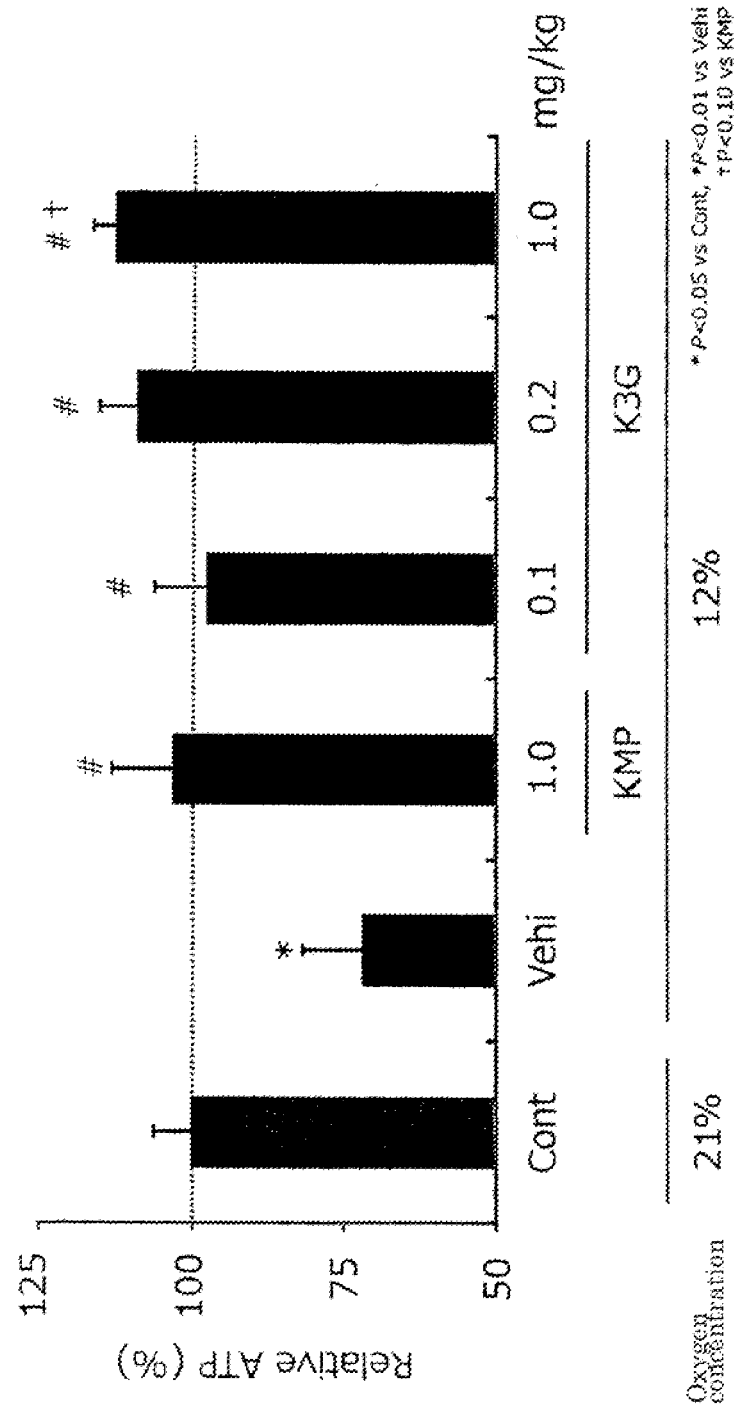

Male Sprague-Dawley rats at 9 weeks of age were orally administered kaempferol (KMP; 1.0 mg/kg body weight) or kaempferol 3-O-glucoside (K3G; 0.1, 0.2, or 1 mg/kg body weight (KMP aglycone equivalent value)) once a day for 8 consecutive days at 9 AM (reared in 21% oxygen). On day 8 of administration, the control group was exposed to 21% oxygen for 1 hour, and the other groups were exposed to 12% oxygen for 1 hour. Then, the soleus muscle (Sol) and whole brain were excised, and the ATP contents in the tissues were measured. The results are shown in FIGS. 9-1 and 9-2.

Test Example 4: Effect on Performance in 400 m Run

A two-group and two-phase crossover study (single ingestion) was conducted for 13 healthy male adults. In the study, a kaempferol-containing capsule-shaped food (SNR 14) wherein the aglycone equivalent value is 10 mg; and a placebo capsule-shaped food: Placebo (kaempferol free) were used as test foods.

Three hours after taking the test food, the subjects sprinted 400 m, and sprinted 400 m again after a 90 minute interval. Respiratory rate and heart rate were monitored during the sprint. The expiratory mouth pressure was measured by the maximum mouth pressure method, before and after the 400 m runs, using an electronic spirometer, autospyro (Minato Medical Science Co., Ltd.).

The subjects inhaled to the limit after three deep breaths in a standing position and then exhaled with full force into the mouthpiece for measurement while preventing air leakage from the nose to determine expiratory mouth pressure.

Figure 10:
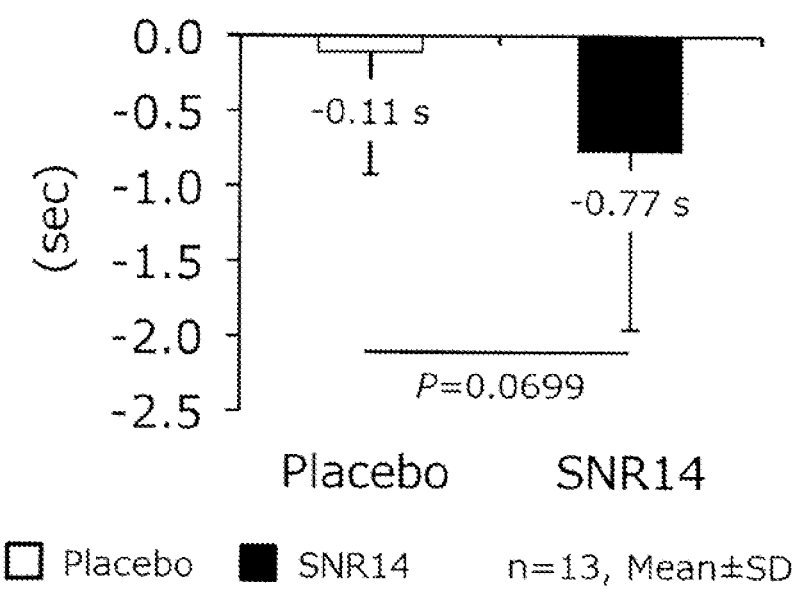
FIG. 10 depicts a graph showing the time changes for the 1st and 2nd 400 m runs.

FIG. 10 depicts a graph showing the time change between the 1st and 2nd 400 m runs. The mean time change of the placebo group was −0.11 seconds and the mean time change of the kaempferol-Ingestion group was −0.77 seconds.

Figure 11:
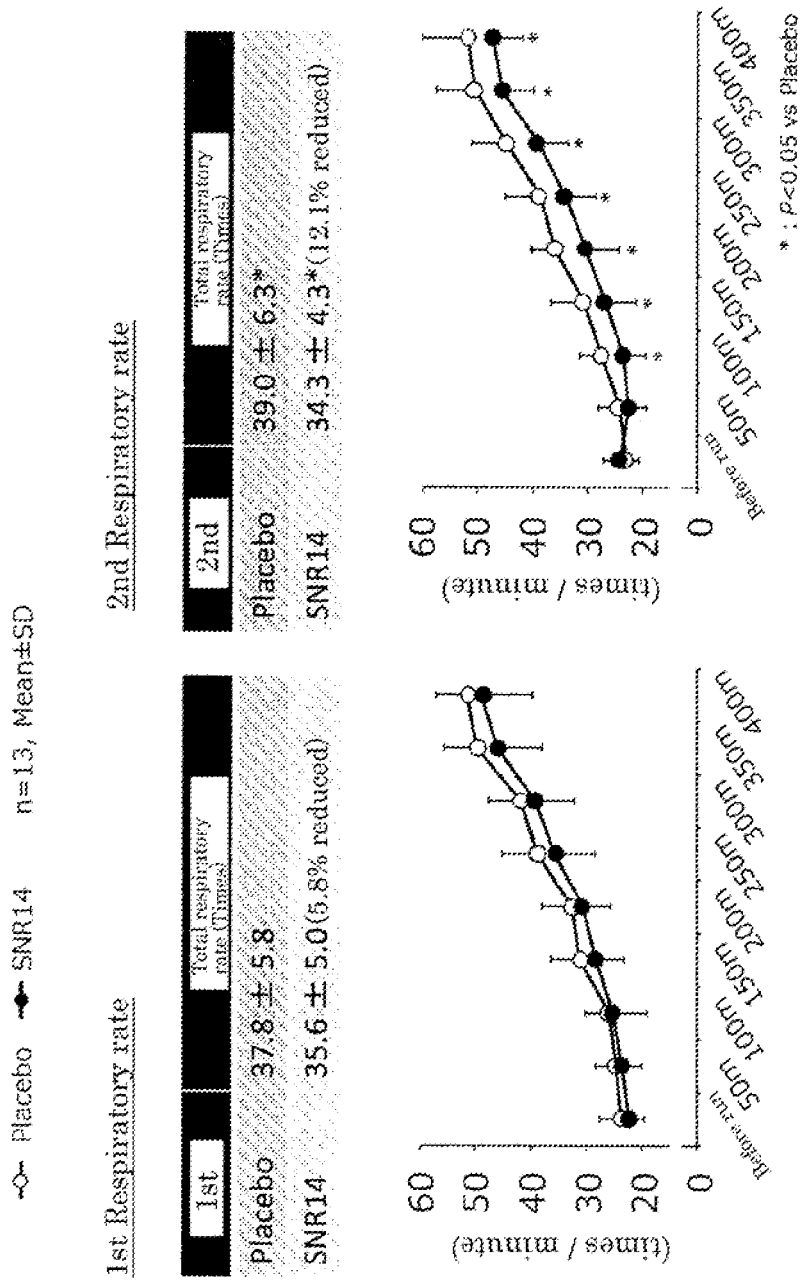
FIG. 11 depicts a graph showing the respiratory rate during 400 m runs.

FIG. 11 depicts a graph showing the respiratory rate during the run.

In the 2nd run, the total number of breaths during the run was significantly lower in the kaempferol-containing food group compared with the placebo food group, and the respiratory rate (times per minute) every 50 m was also significantly lower in the kaempferol-containing food group.

Figure 12:
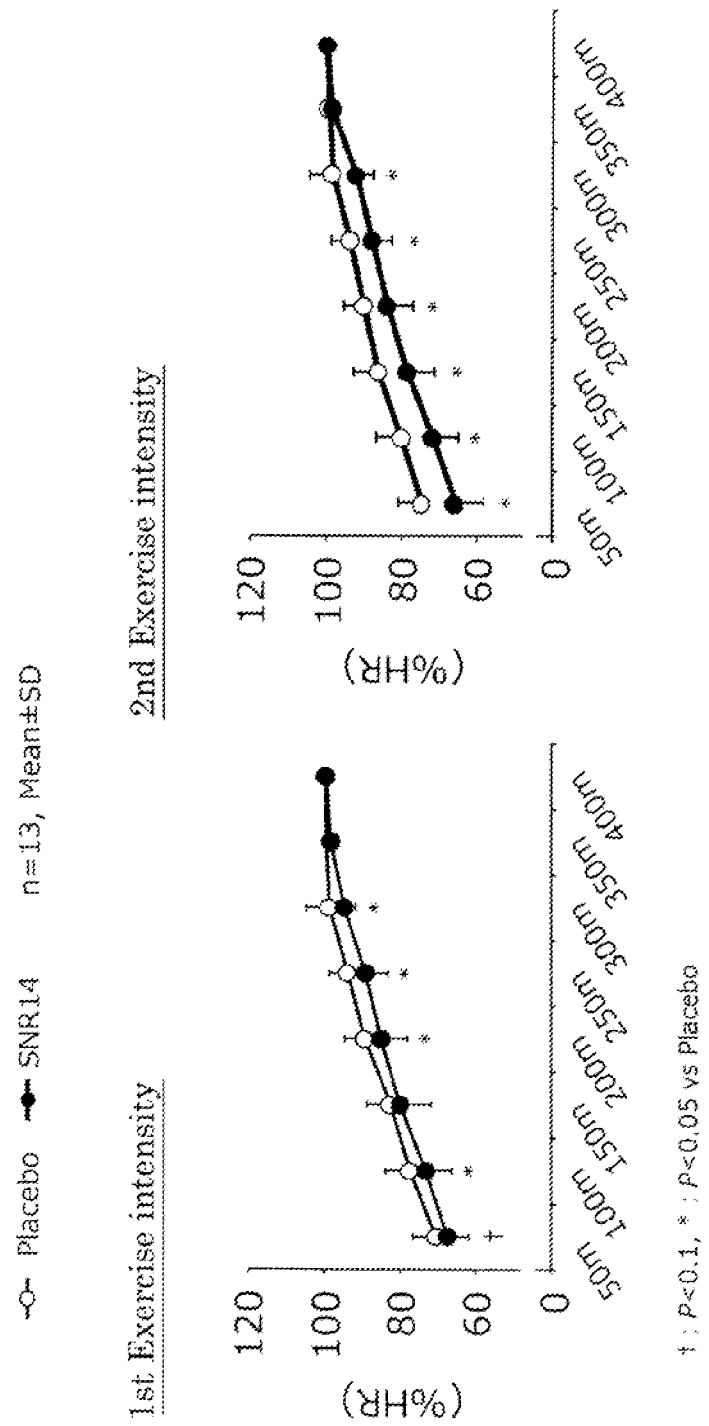
FIG. 12 depicts a graph showing the exercise intensity during sprints.

FIG. 12 depicts a graph showing the exercise intensity during the runs. For the second run, the exercise intensity during the run was significantly lower in the kaempferol-containing food group compared with the placebo food group.

Figure 13:
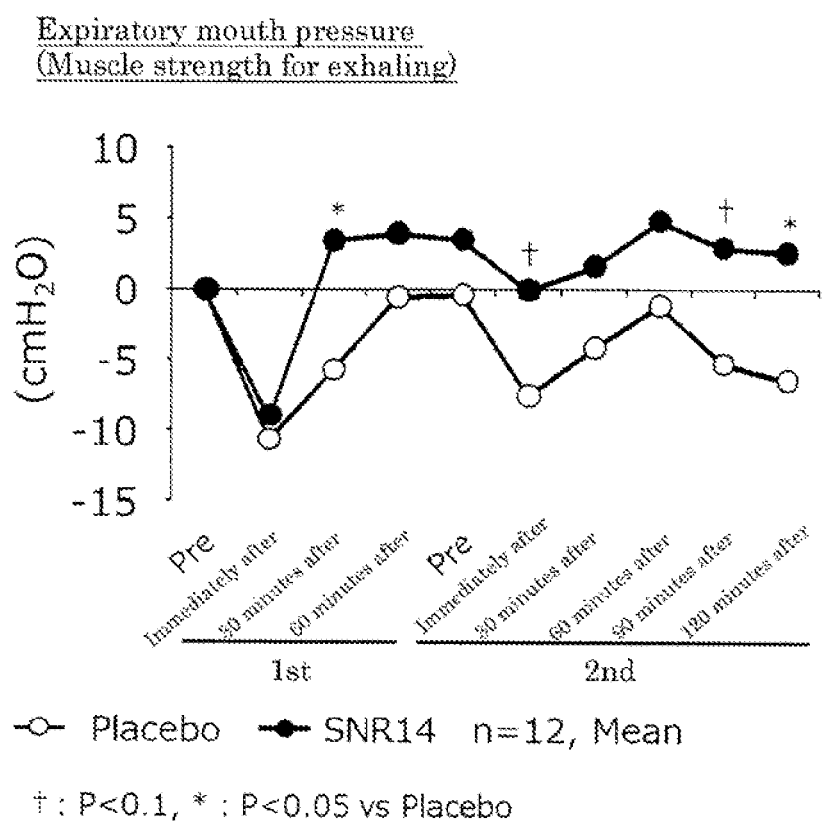
FIG. 13 depicts a graph showing the changes in expiratory mouth pressures.

FIG. 13 shows a graph showing the changes in expiratory mouth pressure. As shown in FIG. 13, the decrease in expiratory mouth pressure was significantly suppressed in the kaempferol-containing food group compared with the placebo food group.

Figure 14:
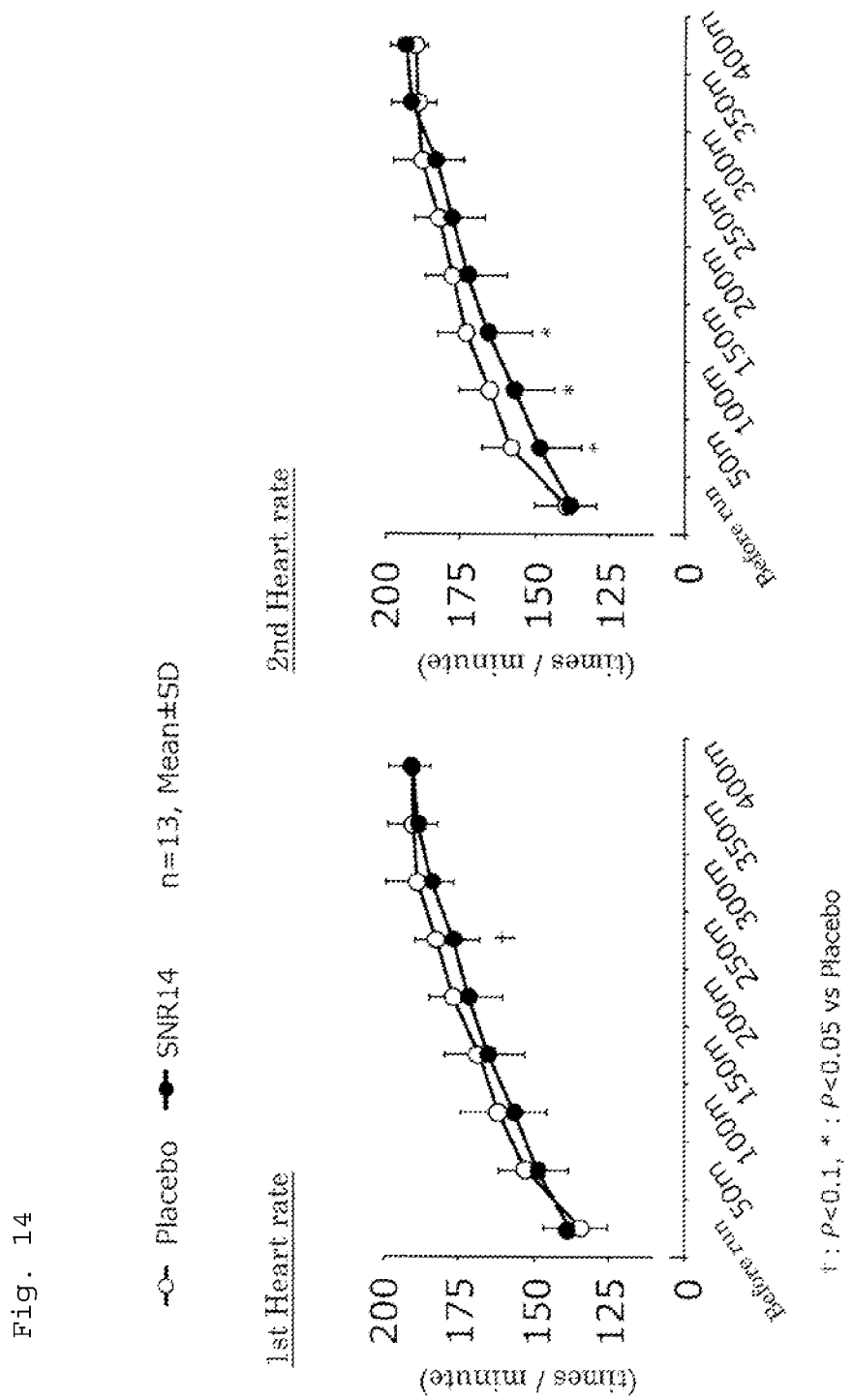
FIG. 14 depicts a graph showing the changes in heart rates.

FIG. 14 depicts a graph showing the changes in heart rate. As shown in FIG. 14, the heart rate was significantly lower at 200-250 m during the 1st run and at 0 (start)-150 m in the 2nd run in the kaempferol-containing food group compared with the placebo food group.

Compared with the placebo group, more participants in the kaempferol-containing food group commented that they felt "comfort", "recovered quickly", "body moved easily".

The kaempferol-containing food may improve exercise performance while giving the feeling of "comfort", "recover quickly" etc.

As shown in the results of Test Example 4, ingestion of kaempferol-containing food decreased the exercise intensity. Furthermore, the ingestion of kaempferol-containing food suppressed the respiratory muscle weakness and the heart rate increase, thereby it is considered that the improvement of breathlessness improves physical activity efficiency and relieves fatigue. In fact, the participants' comments which was that exercise intensity was reduced by the ingestion of kaempferol-containing food suggests that physical activity efficiency was improved, and fatigue was reduced, due to ingestion of kaempferol-containing food. Therefore, it has been suggested that the composition can be used for inhibiting heart rate elevation, reducing breathlessness composition, and/or improving endurance.

The invention claimed is:

1. A method for improving physical activity efficiency, comprising administering a composition comprising a kaempferol analog of Formula I to a subject in need thereof:

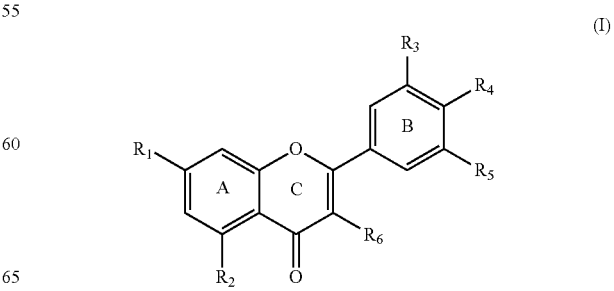

or a glycoside thereof, wherein:
R$_1$ is —OH;
R$_2$ is —OH;
R$_3$ is H;
R$_4$ is —OH;
R$_5$ is H; and
R$_6$ is —OH; and
wherein the composition is administered orally at a dose of 0.1 mg to 50 mg (kaempferol analog equivalent value) of the kaempferol analog or a glycoside thereof per day.

2. The method according to claim 1, wherein the improvement in physical activity efficiency is improvement in endurance.

3. The method according to claim 1, wherein the improvement in physical activity efficiency is reduction of breathlessness.

4. The method according to claim 1, wherein the glycoside of kaempferol analog is represented by Formula I, wherein:
at least one selected from R$_1$, R$_2$, R$_4$, and R$_6$ is independently selected from —OR$_7$, —OR$_7$R$_8$, and —OR$_7$R$_8$R$_9$;
R$_7$ is a glucose residue; and
R$_8$ and R$_9$ are independently selected from a glucose residue, a mannose residue, a galactose residue, a fucose residue, a rhamnose residue, an arabinose residue, a xylose residue, a fructose residue, a glucuronic acid residue, and an apiose residue.

5. The method according to claim 1, wherein the kaempferol analog or a glycoside thereof is kaempferol or kaempferol 3-O-glucoside.

6. The method according to claim 1, wherein the composition comprises 0.1 to 50 mg (kaempferol analog equivalent value) of the kaempferol analog or a glycoside thereof.

7. The method according to claim 1, wherein the composition comprises 0.5 mg to 50 mg (kaempferol analog equivalent value) of the kaempferol analog or a glycoside thereof.

8. The method according to claim 1, wherein the composition is administered orally at a dose of 1 mg to 50 mg (kaempferol analog equivalent value) of the kaempferol analog or a glycoside thereof per administration.

9. The method according to claim 1, wherein the composition is administered orally at a dose of 0.5 mg to 50 mg (kaempferol analog equivalent value) of the kaempferol analog or a glycoside thereof per administration.

10. The method according to claim 1, wherein the composition is administered orally at a dose of 1 mg to 30 mg (kaempferol analog equivalent value) of the kaempferol analog or a glycoside thereof per day.

11. The method according to claim 1, wherein the composition is administered orally at a dose of 2 mg to 30 mg (kaempferol analog equivalent value) of the kaempferol analog or a glycoside thereof per day.

12. The method according to claim 1, wherein the composition is administered to a subject who is hypoxic.

13. The method according to claim 1, wherein the composition is a food or a drink.

14. The method according to claim 1, wherein the composition is a pharmaceutical composition.

15. A method for reducing fatigue, comprising administering a composition comprising a kaempferol analog of Formula I to a subject in need thereof:

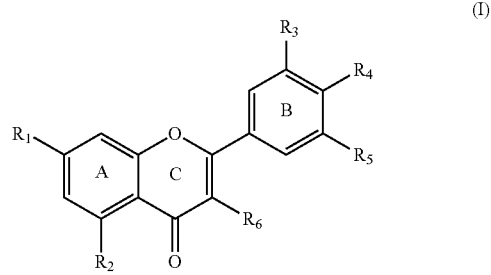

or a glycoside thereof, wherein:
R$_1$ is —OH;
R$_2$ is —OH;
R$_3$ is H;
R$_4$ is —OH;
R$_5$ is H; and
R$_6$ is —OH; and
wherein the composition is administered orally at a dose of 0.1 mg to 50 mg (kaempferol analog equivalent value) of the kaempferol analog or a glycoside thereof per day.

* * * * *